(12) United States Patent
Jiang et al.

(10) Patent No.: US 7,835,003 B2
(45) Date of Patent: Nov. 16, 2010

(54) OPTICAL PH SENSOR

(75) Inventors: Li Jiang, Newton, MA (US); Timothy Gareth John Jones, Cottenham (GB)

(73) Assignee: Schlumberger Technology Corporation, Cambridge, MA (US)

( * ) Notice: Subject to any disclaimer, the term of this patent is extended or adjusted under 35 U.S.C. 154(b) by 384 days.

(21) Appl. No.: 11/791,905

(22) PCT Filed: Dec. 1, 2005

(86) PCT No.: PCT/GB2005/004589

§ 371 (c)(1),
(2), (4) Date: Apr. 21, 2008

(87) PCT Pub. No.: WO2006/059097

PCT Pub. Date: Jun. 8, 2006

(65) Prior Publication Data

US 2009/0009768 A1   Jan. 8, 2009

(30) Foreign Application Priority Data

Dec. 2, 2004  (GB) .................... 0426466.9

(51) Int. Cl.
G01N 21/59 (2006.01)
(52) U.S. Cl. .............. 356/436; 436/528; 435/287.2
(58) Field of Classification Search ......... 356/432–440; 435/7.9, 287.2, 6, 91.2; 436/528
See application file for complete search history.

(56) References Cited

U.S. PATENT DOCUMENTS

| 3,780,575 A | 12/1973 | Urbanosky |
| 3,859,851 A | 1/1975 | Urbanosky |
| 3,904,373 A | 9/1975 | Harper |
| 4,029,597 A | 6/1977 | Neisius et al. |
| 4,200,110 A | 4/1980 | Peterson et al. |
| 4,560,248 A | 12/1985 | Cramp et al. |
| 4,798,738 A | 1/1989 | Yafuso et al. |
| 4,801,655 A | 1/1989 | Murray, Jr. et al. |
| 4,803,049 A | 2/1989 | Hirschfeld et al. |
| 4,849,172 A | 7/1989 | Yafuso et al. |
| 4,994,671 A | 2/1991 | Safinya et al. |
| 5,028,395 A | 7/1991 | Sebille et al. |

(Continued)

FOREIGN PATENT DOCUMENTS

DE      195 22 610 C1    12/1996

(Continued)

OTHER PUBLICATIONS

Baker et al: "The modelling and control of the pH response of an immobilised indicator", Sensors and Actuators B 29, 1995, pp. 368-373.

(Continued)

*Primary Examiner*—Hoa Q Pham
(74) *Attorney, Agent, or Firm*—Vincent Loccisano; James McAleenan; Brigid Laffey

(57) ABSTRACT

An optical sensor for pH is described using a cross-linked network of bisilanes to immobilize a pH sensitive chromophore to a surface potentially exposed to a high pressure, high temperature environment such as wellbore effluents at a downhole location.

18 Claims, 7 Drawing Sheets

U.S. PATENT DOCUMENTS

| | | | |
|---|---|---|---|
| 5,039,492 | A | 8/1991 | Saaski et al. |
| 5,046,028 | A | 9/1991 | Bryan et al. |
| 5,070,158 | A * | 12/1991 | Holloway et al. ........... 525/475 |
| 5,166,990 | A | 11/1992 | Riccitelli et al. |
| 5,236,667 | A | 8/1993 | Puschett et al. |
| 5,351,532 | A | 10/1994 | Hager |
| 5,354,825 | A | 10/1994 | Klainer et al. |
| 5,378,432 | A | 1/1995 | Bankert et al. |
| 5,445,228 | A | 8/1995 | Rathmell et al. |
| 5,517,024 | A | 5/1996 | Mullins et al. |
| 5,650,331 | A | 7/1997 | Jorgensen et al. |
| 5,736,650 | A | 4/1998 | Hiron et al. |
| 5,814,280 | A | 9/1998 | Tomita et al. |
| 5,829,520 | A | 11/1998 | Johnson |
| 6,020,207 | A * | 2/2000 | Liu ............................ 436/164 |
| 6,023,340 | A | 2/2000 | Wu et al. |
| 6,159,695 | A * | 12/2000 | McGovern et al. ............. 435/6 |
| 6,528,264 | B1 * | 3/2003 | Pal et al. ....................... 506/32 |
| 6,558,607 | B1 * | 5/2003 | Winter et al. ............... 264/425 |
| 6,939,717 | B2 | 9/2005 | Jiang et al. |
| 7,195,924 | B2 * | 3/2007 | Hwang ....................... 436/524 |
| 2002/0034580 | A1 * | 3/2002 | Yang et al. ................. 427/2.11 |
| 2002/0192722 | A1 * | 12/2002 | Stolowitz et al. ............. 435/7.9 |
| 2002/0196993 | A1 * | 12/2002 | Schroeder .................... 385/12 |
| 2003/0082588 | A1 * | 5/2003 | Garimella ....................... 435/6 |
| 2003/0134426 | A1 | 7/2003 | Jiang et al. |
| 2005/0028974 | A1 * | 2/2005 | Moody ....................... 166/264 |
| 2005/0109098 | A1 * | 5/2005 | DiFoggio ................. 73/152.55 |
| 2005/0265649 | A1 * | 12/2005 | da Silva et al. ................ 385/13 |

FOREIGN PATENT DOCUMENTS

| | | |
|---|---|---|
| EP | 0 481 740 A2 | 4/1992 |
| EP | 0 481 740 A3 | 4/1992 |
| EP | 0881 241 A2 | 12/1998 |
| EP | 0881 241 A3 | 12/1998 |
| GB | 2 359 631 A | 8/2001 |
| JP | 64-44834 A | 2/1989 |
| WO | WO 99/00575 A2 | 1/1999 |
| WO | WO 99/00575 A3 | 1/1999 |
| WO | WO01/63094 A1 | 8/2001 |
| WO | WO 2004/048969 A1 | 6/2004 |

OTHER PUBLICATIONS

Baldini et al: "Controlled-pore glasses embedded in plastic optical fibers for gastric pH sensing purposes", Applied Spectroscopy, vol. 48, No. 5, 1994, pp. 549-552.

Baldini et al: "In vivo optical-fibre pH sensor for gastro-oesophageal measurements", Sensors and Actuators B 29, 1995, pp. 164-168.

Baldini et al: "An extended-range fibre-optic pH sensor", Sensors and Actuators A, 37-38, 1993, pp. 180-186.

Baldini et al: "Optical-fibre sensors by silylation techniques", Sensors and Actuators B, 11, 1993, pp. 353-360.

Baldini et al: "Adsorption-based optical transduction in optical fibre chemical sensors for environmental and industrial applications", Adsorption and its Applications in Industry and Environmental Protection, Studies in Surface Science and Catalysis, vol. 120, 1998, pp. 925-948.

Bierbaum et al: "A near edge x-ray absorption fine structure spectroscopy and x-ray photoelectron spectroscopy study of the film properties of self-assembled monolayers of organosilanes on oxidized Si(100)", Langmuir, 11, 1995, pp. 512-518.

Bishop: "Theory and principles of visual indicators", Indicators, Pergamon, Oxford, 1972, pp. 13-15 and 62-63.

Boisde et al: "Co-immobilization of several dyes on optodes for pH-measurements", SPIE Chemical and Medical Sensors, vol. 1510, 1991, pp. 80-94.

Boisde et al: "pH measurements with dyes co-immobilization on optodes: principles and associated instrumentation", Int. Journal of Optoelectronics, vol. 6, No. 5, 1991, pp. 407-423.

Brzoska et al: "Silanization of solid substrates: A step toward reproducibility", Langmuir, 10, 1994, pp. 4367-4373.

Byrne et al: "High precision multiwavelength pH determinations in seawater using cresol red", Deep-Sea Research, vol. 36, No. 5, 1989, pp. 803-810.

Byrne et al: "Seawater pH measurements: an at-sea comparison of spectrophotometric and potentiometric methods", Deep-Sea Research, vol. 35, No. 8, 1988, pp. 1405-1410.

Cammann: "Opt(R)ode quo vadis?", Sensors and Actuators B 51, 1998, pp. 1-4.

Carey et al: "Polymer-coated cylindrical waveguide absorption sensor for high acidities", Anal. Chem. 61, 1989, pp. 1674-1678.

Cheng et al: "Investigation of the photoelectric conversion of a novel molecule (E)-N-methyl-4-{2-[4-(dihexadecylamino) phenyl]ethenyl}pyridazinium iodide, in LB films fabricated on an $SnO_2$ electrode", J. Mater. Chem. 7(4), 1997, pp. 631-635.

Chovelon et al: "Silanization of stainless steel surfaces: influence of application parameters", J. Adhesion, vol. 50, 1995, pp. 43-58.

Citterio et al: "Dyes for use in integrated optical sensors", Sensors and Actuators B 38-39, 1997, pp. 202-206.

Clayton et al: "Spectrophotometric seawater pH measurements: total hydrogen ion concentration scale calibration of m-cresol purple and at-sea results", Deep-Sea Research, vol. 40, No. 10, pp. 2115-2129, 1993.

Deboux et al: "A robust and miniature optical fibre pH sensor based on methylene blue dye adsorption", SPIE, vol. 2542, 1995, pp. 167-176.

Degrandpre et al: "Calibration-free optical chemical sensors", Anal. Chem., 71, 1999, pp. 1152-1159.

Ding et al: "Direct pH measurement of NaCl-bearing fluid with an in situ sensor at 400°C and 40 megapascals", Science, vol. 272, 1996, pp. 1634-1636.

Ding et al: "Fibre optic pH sensors prepared by sol-gel immobilisation technique", Electronics Letters, vol. 27, No. 17, 1991, pp. 1560-1562.

Draxler et al: "pH sensors using fluorescence decay time", Sensors and Actuators B, 29, 1995, pp. 199-203.

Dreyfuss et al: "Chemistry of silane coupling reactions. 2. Reaction of dimethylmethoxysilanated poly(butadiene) with triethylsilanol and with glass", Macromolecules, vol. 11, No. 5, 1978, pp. 1036-1038.

Dybko et al: "Novel matrix for fibre optic chemical sensors made of particle track polymer", SPIE vol. 2508, 1995, pp. 351-357.

Dybko et al: "Efficient reagent immobilization procedure for ion-sensitive optomembranes", Sensors and Actuators B 38-39, 1997, pp. 207-211.

Dybko et al: "Polymer track membranes as a trap support for reagent in fiber optic sensors", J. Appl. Polym. Sci., 59, 1996, pp. 719-723.

Feely et al: "Composition and dissolution of black smoker particulates from active vents on the Juan de Fuca Ridge", Journal of Geophysical Research, vol. 92, No. B11, 1987, pp. 11,347-11,363.

Galster: "Other methods of pH measurement", pH Measurement: Fundamentals, Methods, Applications, Instrumentation, VCH Publishers, 1991, pp. 222-227.

Gonzalez-Benito et al: "Surface characterization of silanized glass fibers by labeling with environmental sensitive fluorophores", J. App. Poly. Sci., 62, 1996, pp. 375-384.

Goss et al: "Application of (3-mercaptopropyl)trimethoxysilane as a molecular adhesive in the fabrication of vapor-deposited gold electrodes on glass substrates", Anal. Chem., 63, 1991, pp. 85-88.

Grattan et al: "Use of sol-gel techniques for fibre optic sensor applications", Sensors and Actuators A, 25-27, 1991, pp. 483-487.

Harper: "Reusable glass-bound pH indicators", Analytical Chemistry, vol. 47, No. 2, 1975, pp. 348-351.

Harrick: "Principles of internal reflection spectroscopy", Internal Reflection Spectroscopy, Interscience Publishers, John Wiley & Sons, 1967, pp. 13-35.

Haruvy et al: "Supported sol-gel thin-film glasses embodying laser dyes. 3. Optically clear $SiO_2$ glass thin films prepared by the fast sol-gel method", Chem. Mater. 4. 1992, pp. 89-94.

Hayert et al: "A simple method for measuring the pH of acid solutions under high pressure", J. Phys. Chem. A, 103, 1999, pp. 1785-1789.

Hickman et al: "Molecular self-assembly of two-terminal, voltammetric microsensors with internal references", Science, vol. 252, 1991, pp. 688-691.

Hisamoto et al: "Theory and practice of rapid flow-through analysis based on optode detection and its application to pH measurement as a model case", Anal. Chem., 68, 1996, pp. 3871-3878.

Hisamoto et al: "Molecular design, characterization and application of multi-information dyes for multi-dimensional optical chemical sensing. Molecular design concepts of the dyes and their fundamental spectral characteristics", Analytica Chimica Acta 373, 1998, pp. 271-289.

Hisamoto et al: "Molecular design, characterization and application of multiinformation dyes for multidimensional optical chemical sensings. 2. Preparation of the optical sensing membranes for the simultaneous measurements of pH and water content in organic media", Anal. Chem. 70, 1998, pp. 1255-1261.

Hisamoto et al: "Molecular design, characterization and application of multi-information dyes (MIDs) for optical chemical sensings. 3. Application of MIDs for λmax-tunable ion-selective optodes", Anal. Chem. 71, 1999, pp. 259-264.

Iler: "The surface chemistry of silica", The Chemistry of Silica. Solubility, polymerization colloid and surface properties, and biochemistry, John Wiley & Sons, New York 1979, pp. 624-637.

Kaasa et al: "Alkalinity in oil field waters. What alkalinity is and how it is measured", 1997 SPE International Symposium on Oilfield Chemistry, Houston, Texas, Feb. 18-21, 1997. SPE 37277.

Kallury et al: "Effect of surface water and base catalysis on the silanization of silica by (aminopropyl) alkoxysilanes studied by x-ray photoelectron spectroscopy and 13C cross-polarization/magic angle spinning nuclear magnetic resonance", Langmuir, 10, 1994, pp. 492-499.

Kelland et al: "Overview of the scale challenges facing the oil and gas industry", Advances in Solving Oilfield Scaling, Aberdeen 1998.

Kohls et al: "Development and comparison of pH microoptodes for use in marine systems", SPIE, vol. 2978, 1997, pp. 82-91.

Koncki et al: "Optical chemical sensing based on thin films of Prussian Blue", Sensors and Actuators B, 51, 1998, pp. 355-358.

Koncki et al: "Composite films of Prussian Blue and N-substituted polypyrroles: Fabrication and application to optical determination of pH", Anal. Chem., 70, 1998, pp. 2544-2550.

Lang et al: "Relationship between structures and photocurrent generation properties in a series of hemicyanine congeners", J. Phys. Chem. B, 102, 1998, pp. 1424-1429.

Le Grange et al: "Effects of surface hydration on the deposition of silane monolayers on silica", Langmuir, 9, 1993, pp. 1749-1753.

Lehmann et al: "Fiber-optic pH meter using NIR dye", Sensors and Actuators B 29, 1995, pp. 392-400.

Liu et al: "Aggregation of a charged dye in monolayer on the subphase containing heparin and in LB multilayers", Journal of Colloid and Interface Science, 203, 1998, pp. 41-46.

Lobnik et al: "pH optical sensors based on sol-gels: Chemical doping versus covalent immobilization", Analytica Chimica Acta, 367, 1998, pp. 159-165.

Mills et al: "Equilibrium studies on colorimetric plastic film sensors for carbon dioxide" Anal. Chem., 64, 1992, pp. 1383-1389.

Nivens et al: "A fiber-optic pH sensor prepared using a base-catalyzed organo-silica sol-gel", Analytica Chimica Acta, 376, 1998, pp. 235-245.

Noire et al: "Optical sensing of high acidity using a sol-gel entrapped indicator", Sensors and Actuators B 51, 1998, pp. 214-219.

Peterson et al: "Fiber optic pH probe for physiological use", Anal. Chem. 52, 1980, pp. 864-869.

Plueddemann: "Chemistry of silane coupling agents", Silane Coupling Agents, Second Edition, Plenum Press, New York, 1991, Chapter 2, pp. 31-54.

Robert-Baldo et al: "Spectrophotometric determination of seawater pH using phenol red", Anal. Chem., 57, 1985, pp. 2564-2567.

Saavedra et al: "Integrated optical attenuated total reflection spectrometry of aqueous superstrates using prism-coupled polymer waveguides", Anal. Chem., 62, 1990, pp. 2251-2256.

Safavi et al: "Optical sensor for high pH values", Analytica Chimica Acta, 367, 1998, pp. 167-173.

Sanchez-Cortes et al: "pH-dependent adsorption of fractionated peat humic substances on different silver colloids studied by surface-enhanced Raman spectroscopy" Journal of Colloid and Interface Science, 198, 1998, pp. 308-318.

Schlageter et al: "High sensitive detection of pH with photoacoustic as an analytical tool", J. Inf. Recording, vol. 23, 1996, pp. 197-199.

Silberzan et al: "Silanation of silica surfaces. A new method of constructing pure or mixed monolayers". Langmuir, 7, 1991, pp. 1647-1651.

Sotomayor et al: "Evaluation of fibre optical chemical sensors for flow analysis systems", Sensors and Actuators B 51, 1998, pp. 382-390.

Spichiger-Keller: "Optical sensors, optodes", Chemical Sensors and Biosensors for Medical and Biological Applications, Wiley-VCH, Weinheim, 1998, chapter 6.

Bernard et al: "Stark effect in hole-burning spectra of dye-doped Langmuir-Blodgett films", Thin Solid Films, 217, 1992, pp. 178-186.

Tamura et al: "Spectrophotometric analysis of the relationship between dissociation and coloration, and of the structural formulas of phenolphthalein in aqueous solution", Analytical Sciences, vol. 12, 1996, pp. 927-930.

Weigl et al: "Capillary optical sensors", Anal. Chem. 66, 1994, pp. 3323-3327.

Werner et al: "Novel optical pH-sensor based on a boradiaza-indacene derivative", Fresenius J. Anal. Chem. 359, 1997, pp. 150-154.

Wu et al: "Adsorption of dyes on nanosize modified silica particles", Journal of Colloid and Interface Science, 195, 1997, pp. 222-228.

Wu et al: "Photoelectric response from two amphiphilic nitrobenzene dyes with alkoxyl on a monolayer-modified ITO electrode", Langmuir, 14, 1998, pp. 3783-3787.

Xia et al: "Photoelectric conversion from a hemicyanine dye containing zinc complex in a Langmuir-Blodgett film", Langmuir, 13, 1997, pp. 80-84.

Xia et al: "Photoelectric response from a stilbazolium dye in a Langmuir-Blodgett film-modified SnO2 electrode", J. Chem. Soc. Faraday Trans., 92(17), 1996, pp. 3131-3135.

Xu et al: "A novel fiber-optic pH sensor incorporating carboxy SNAFL-2 and fluorescent wavelength-ratiometric detection", J. Biomed. Mater. Res. 39, 1998, pp. 9-15.

Yamaguchi et al: "Molecular structure of the zwitterionic form of phenolsulfonphthalein", Analytical sciences, vol. 13, 1997, pp. 521-522.

Yang et al: "Chemical sensing using sol-gel derived planar waveguides and indicator phases", Anal. Chem., 67, 1995, pp. 1307-1314.

Yang et al: "Growth of ultrathin covalently attached polymer films: Uniform thin films for chemical microsensors", Langmuir, vol. 14, No. 7, 1998, pp. 1505-1507.

* cited by examiner

OPTICAL PH SENSOR

The invention relates to an optical pH sensor for use in a wellbore and corresponding methods for analyzing of fluids produced from subterranean formations. More specifically, it relates to an optical pH sensor attached to drillpipe, wireline and/or production logging tools for in-situ analysis of effluents produced from subterranean formation.

CROSS-REFERENCE TO RELATED APPLICATIONS

This application claims the benefits of priority from:
i) Application Number 0426466.9, entitled "OPTICAL pH SENSOR," filed in the United Kingdom on Dec. 2, 2004; and
ii) Application Number PCT/GB2005/004589, entitled "OPTICAL pH SENSOR," filed under the PCT on Dec. 1, 2005;

All of which are commonly assigned to assignee of the present invention and hereby incorporated by reference in their entirety.

BACKGROUND OF THE INVENTION

Analyzing samples representative of downhole fluids is an important aspect of determining the quality and economic value of a hydrocarbon formation.

As the technology of oil and gas production advances, and environmental regulations become stricter, new demands are put on the industry to identify more cost-effective methods of reservoir control. A leading example of such control is the prediction, monitoring, preventing and removal of scale formation. A key request that directly related to the first three operations is in situ measurement of pH, together with the concentration of the critical ions, in aqueous borehole fluids. In particular, real time measurement of pH will offer valuable prediction of the initiation of nucleation that eventually leads to macroscopic scale formation. Also, in the ever-significant operation of in situ $H_2S$ detection, it is often a prerequisite that medium pH is known so that total inorganic sulfur can be deduced on the basis of thermodynamic equilibrium.

Present day operations obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or through one or more sensors mounted on the drillstring. The latter method, where successfully implemented, has the advantage of obtaining data while drilling, whereas the former installation could provide additional value as part of a control system for wellbores and hydrocarbon production therefrom.

To obtain an estimate of the composition of downhole fluids, the MDT tools uses an optical probe to estimate the amount of hydrocarbons in the samples collected from the formation. Other sensors use resistivity measurements to discern various components of the formations fluids.

General downhole measurement tools for oilfield applications are known as such. Examples of such tools are found in the U.S. Pat. Nos. 6,023,340; 5,517,024; and 5,351,532 or in the International Patent Application WO 99/00575.

Rapid and reliable pH measurement at downhole conditions, i.e., elevated temperature and pressure, and the presence of multiphase fluids, represents a formidable challenge to the existing techniques, such as potentiometric measurement of electromotive force based on glass electrodes, due to their poor stability and difficulty in interface renewal.

Although, their responses to changes in ionic composition are much faster than with potentiometric methods, conventional calorimetric methods using homogeneous reactions with indicator dyes often suffer from a lack of precision.

The measurement of pH is an art with an extended track record. The mainstream techniques are colorimetry and potentiometry, while most of those relevant to the present work involving entrapping dye molecules into thick polymeric films. In a review article, Cammann outlined the current scope and directions of future development for optical chemical sensors, in particular, for pH applications in: K. Cammann, "Optrode quo vadis?", Sensors and Acutators B, 51, 1(1998), while Spichiger-Keller presented the fundamental principles of optical chemical sensors in: U. E. Spichiger-Keller, "Chemical sensors and biosensors for medical and biological applications", Chapter 6(259-320) Wiley-VCH, Weinheim, 1998.

Apart from the entrapment into films, a variety of other methods based on either physical and chemical adsorption are used to immobilize the active (color changing) species. The known methods include sol-gel processes or bifunctional agents to bind the active species to a solid substrate.

Where optical transducers are applied to measure the response of the sensor to illumination, absorbance or transmission measurements can be used. In many cases, a fluorescence signals is monitored. Alternatively, it is known to use evanescent light or total internal reflection (TIR) measurements to detect a change in the optical properties of the active species. Another possible detection mechanism is based on surface plasmon resonance (SPR). Many of the above methods are used together with fiber optics to couple light into the system and connect light source, sensor and optical detector.

In modifying siliceous or metal oxide surfaces, one technique that has been used is derivatization with bifunctional silanes, i.e., silanes having a first functional group enabling covalent binding to the surface (often an Si-halogen or Si-alkoxy group, as in —SiCl3 or —Si(OCH3)3, respectively) and a second functional group that can impart the desired chemical and/or physical modifications to the surface. This process is generally referred to as silylation.

Silylation has been used for optical pH sensing purpose and is for example described by F. Baldini et al. in: F. Baldini and S. Bracci, "Optical-fibre sensors by silylation techniques", Sensors and Actuators B, 11, 353(1993) using bromophenol blue as chromophore immobilized on controlled-pore glasses (CPG).

Calibration of pH sensors is a challenging issue. In one known approach a pH-independent wavelength is monitored while probing wavelengths where the entrapped dye indicator showed maximal transmittance. In addition to the wavelength where the variation of analyte's concentration is probed, another wavelength was probed, which is unaffected by the measurement but is subject to other intrinsic changes in the rest of the system, such as light source fluctuation and/or changes in optical fiber transmission mode. The latter changes are common at both wavelengths and can hence be eliminated. A pH sensor designed as such, using physically adsorbed methylene blue on the tip of an optical fibre, resulted in a rather wide pH range of 3-10 with a resolution of 0.015 units. An extra advantage of this "calibration-free" approach is the dampened temperature dependence of the resultant device, due to similar coefficient of the individual molar adsorptivities.

Though mature and effective in their own right, none of these aforementioned techniques is capable of direct applications to elevated temperature, high pressure and complex chemical compositions. The device that was able to operate in conditions most closely resemble those encountered in oilfield industry was an in situ pH sensor for hydrothermal fluids, as reported by Ding and co-worker in: K. Ding and W. E. Seyfried, Jr., "Direct pH measurement of NaCl-bearing fluid with an in situ sensor at 400° C. and 40 megapascals", *Science*, 272, 1634(1996). Using a yttria-stablized zirconia membrane as the working electrode, they measured the potentiometric change as a result of pH variation under supercritical conditions. But this approach suffered from the slow response time (>20 minutes) and lack of stability, where the Ag/AgCl reference electrode was in direct contact with the fluids. Also, Gervais et al designed a pH sensor, using a fluorescein indicator, which was able to operate at pressure up to 250 MPa, as described in: M. Hayert, J-M Perrie-Cornet and P. Gervais, "A simple method for measuring the pH of acid solutions under high pressure", *J. Phys. Chem. A.* 103, 1785(1999). The measurement of pH under wellbore conditions is made even more complex because of the pressure induced dissociation of weak acids. For example, neutral water undergoes a shift of about –0.73 pH/100 MPa.

More recently a method for pH measurement under downhole condition has been described in the published international patent application WO 2004/048969 A1. A colorant is added to a sample taken by a downhole monitoring system suspended into the wellbore from a wireline. The color change of the colorant is monitored by a suitable spectral analyzer and can be made indicative of, for example, the pH of the sample fluid.

Whilst there are numerous examples of optical pH sensors in other technical fields such as physiological application, the oilfield industry lacks simple and robust sensor to measure the pH under downhole conditions. It is therefore an object of the present invention to provide a sensor for pH measurement at high pressure and/or high temperatures. It is a further object of the present invention to provide downhole sensors and sensing methods for pH.

SUMMARY OF THE INVENTION

The invention describes a pH detection system based on the chemical immobilisation of a monolayer of chromophoric indicators, in a uniform orientation, onto a transparent substrate via a two-step reaction scheme. The coupling chemistry is based on bisilane agents, particularly bi-functional organosilane agents, where one terminal functional group self-assembles onto the substrate and forms a cross-linked network that stabilizes these molecules, while the other silane group is available for the binding of target dye indicators. Changes in the indicators' UV or visible spectra such as UV or visible spectra, as a result of pH variation, are probed, preferably via a spectrometer set up, to monitor an amplified internal reflectance signal of the absorbance.

In a preferred embodiment, molecular scale membranes are applied to readily manipulate the surface wettability towards water and oil phase, while affording additional protection from fouling to the reactive centers.

The detection scheme is arranged to have little temperature dependence and dependence on the indicator concentration or optic path length of the internal reflectance element (IRE).

Such a system may be assembled into an appropriate tool for continuous measurement of pH, and derived therefrom other species or compounds such as $P_{CO2}$, of borehole fluids in either wireline and/or production logging processes.

Preferably assembled as a rugged, no-moving-parts device, such a sensor can be readily integrated into a drill string, production logging tool and open hole formation tester tool such as the MDT™ tool of Schlumberger.

These and other features of the invention, preferred embodiments and variants thereof, possible applications and advantages will become appreciated and understood by those skilled in the art from the following detailed description, appended drawings and claims.

DETAILED DESCRIPTION OF THE INVENTION

The concentration of protons in an aqueous medium arises from the chemical equilibrium of water molecules presented in equation 1 and the definition of pH is given in equation 2:

$$pH=-\log[H^+] \quad [2]$$

The alteration of the colors of dyes by the interactions with acids and/or alkalines is one of the oldest observations in chemistry. The color change results from a rearrangement of the indicator molecules when hydrogen ions are (partially) released or taken up. Typical indicator molecules or chromophores have two tautomeric forms, each having a different absorption spectrum. As the pH of the solution varies, the relative size of each tautomer's optical absorption peak changes in proportion to the changing relative concentration of the two individual forms.

The present invention employs a unique approach for interface modification, that is, using a bi-functional organosilane reagent. In the example an alkyl chain is used terminated at each end with a group according to the formula —SiX3 where X can be am alkoxy-group (e.g. —OMe or OEt) or a halogen (e.g. —Cl or Br).

Figure 1A:
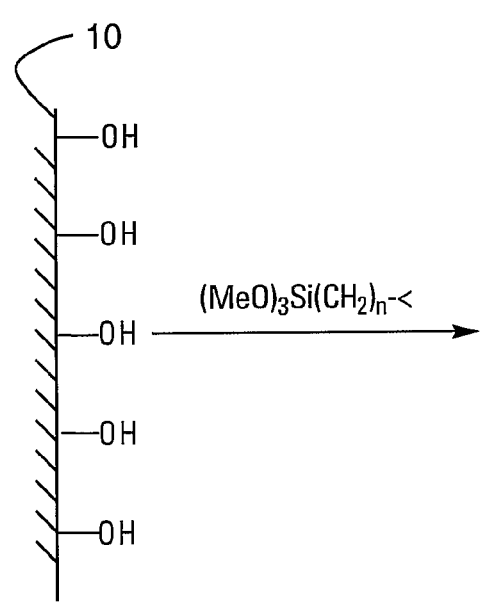
FIGS. 1A-1D illustrate the preparation of a transparent carrier with a cover layer of chromophores in accordance with an example of the invention.

As shown in FIG. 1A, one terminal functional group binds to the surface of a transparent substrate or carrier 10, e.g. glass, treated with a mixture of sulfuric acid and hydrogen peroxide to enhance the number of reactive sites (—OH).

Figure 1B:
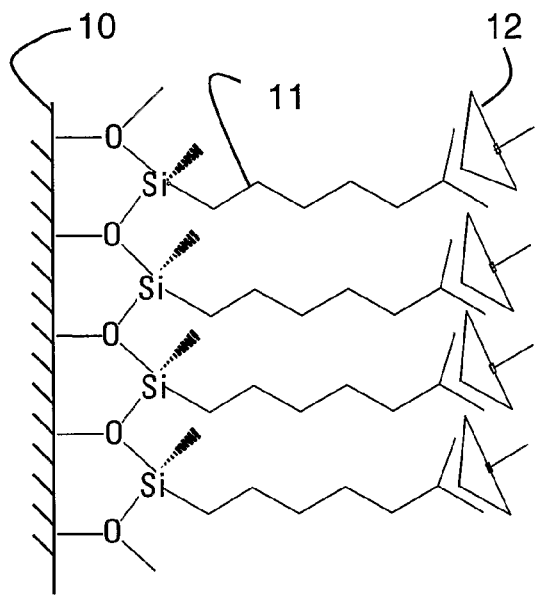

The surface 10 is then exposed to alkoxy-terminated ((MeO)$_3$) bi-functional silane 11. In FIG. 1B, the silane is shown linked to the surface. The chemistry of the binding mechanism is thought to be analogous to the reaction

where X denotes one of the terminal groups.

The other functional group (-<) subsequently binds to the chromophore 12 via a condensation reaction with its hydrolysable group. Such silane reagents involved in the formation of covalent bonds offer a bridge between inorganic surfaces and organic species, and are stable in both thermal and temporal terms. Ordinary silane bonds are known to survive up to 500° C. in water vapor over a period of 1000 hours. The effective coverage of the silane reagents at the interface provides a marked improvement in composite properties and, hence, substantially extends the lifetime of the modification layer leading ultimately to a much-improved long-term stability under harsh conditions. These properties are described for example in: G. B. Harper, "Reusable glass-bound pH indicators", *Anal. Chem.,* 47, 348(1975).

Figure 1C:
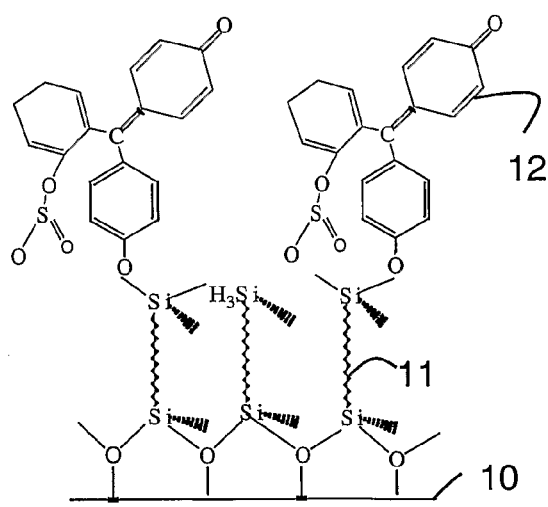

In the example of FIG. 1C, the active species or chromophore 12 of FIG. 1B is a phenolsulphonphthalin also referred to as Phenol Red. The Phenol Red molecules are chemically immobilized in a uniform orientation as a single layer at the interface. It should be understood that many similar chromophores are known in the art and it is considered being a mere matter of adaptation to use chromophores other than Phenol Red for the purpose of this invention.

Figure 1D:
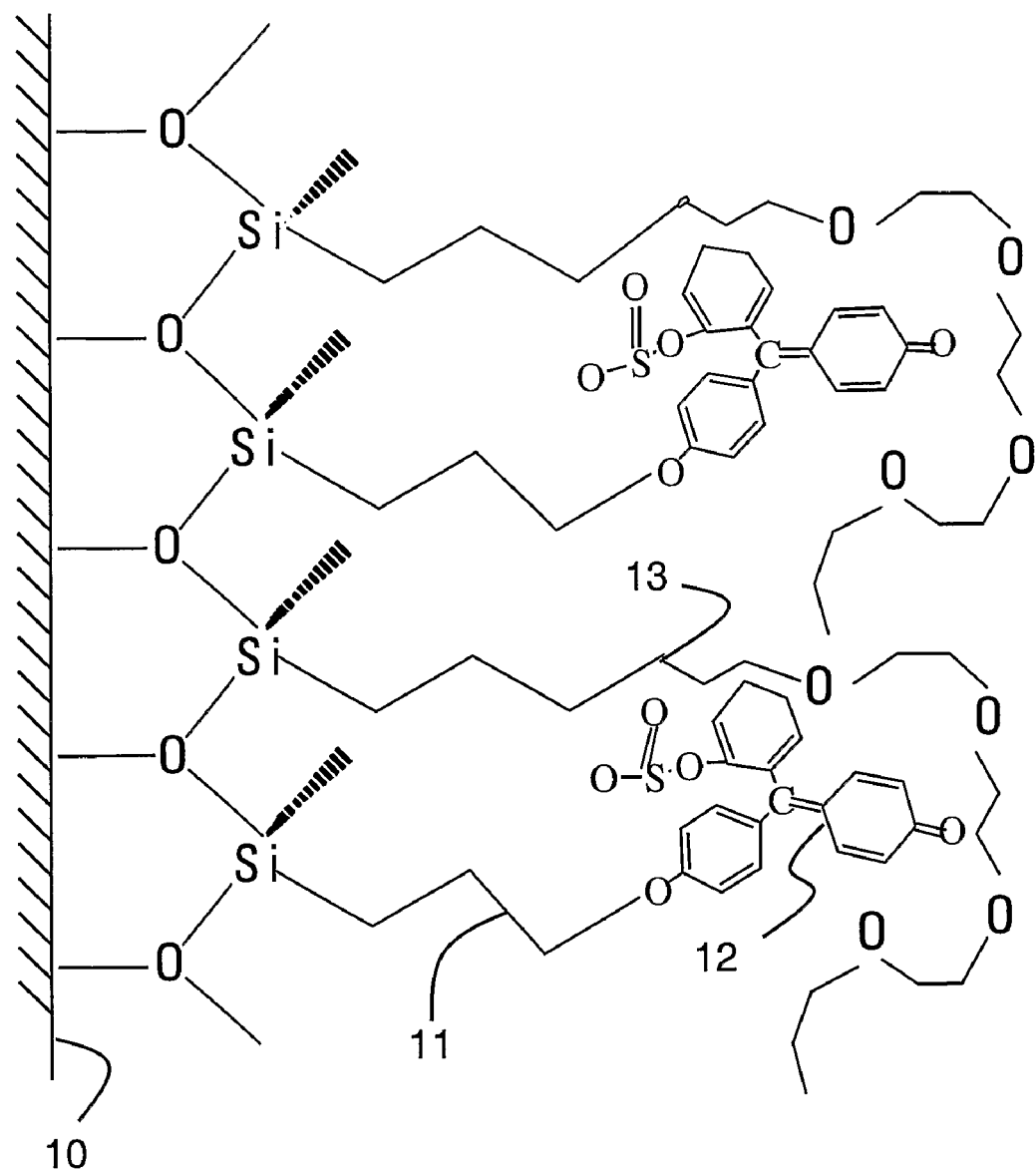

The adaptation of the surface 10 to a specific purpose can be further enhanced. In the example of FIG. 1D, molecular (scale) membranes are added to provide an effective protection for the chromophores 12. The interfacial wettability is manipulated towards a specific phase. For example, long chain molecules 13 terminated with polyethylene glycol, co-adsorbed alongside the indicators and usually in the (stretched) length range of 9-16 nm, result in a robust hydrophilic surface. Likewise, hydrophobicity may be obtained using pure hydrocarbon chains terminated with methyl groups. In addition to enhancing the sampling procedure in the target phase, these membranes 13 also offer effective protection for the reactive centers from fouling. As experiments show, the interfacial chromophores remain functional after experiencing extended reflux up to temperatures of ~160° C. in the mixture of crude oil, high salinity water, surfactant and solid particles.

Figure 2:
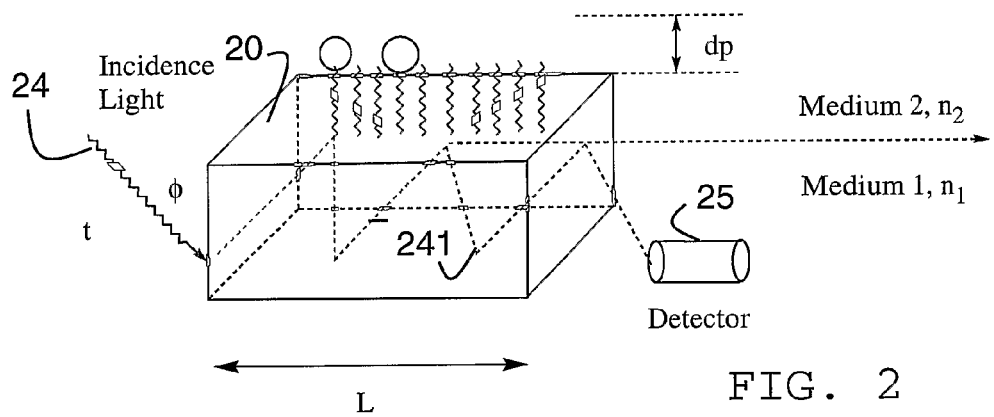
FIG. 2 shows elements of a sensor in accordance with an example of the invention.

The mono-molecular layered interfacial structures constructed in accordance with the invention are interrogated using an optical system such as the spectrophotometer outlined in FIG. 2. The device probes the change in the optical absorption in an internal reflectance mode. Thus, light 24 from a suitable light source (e.g. a light emitting diode, not shown) generates internally reflected optical waves 241 propagating through the carrier 20 and its modified interface. The amplitude of the evanescent wave of light decays exponentially with distance from the interface and hence the sensitivity is confined within a thin surface layer. The depth of penetration, defined as the distance where the intensity of the evanescent oscillation falls to $e^{-1}$ of its value at the interface, is given as below:

$$d_p = \lambda_1 / 2\pi (\sin^2 \phi - n^2)^{1/2} \quad [3]$$

where $\lambda_1$ ($=\lambda_0/n_1$) is the wavelength of the incidence light entering the optical window (medium 1, optically denser) at an angle $\phi$ and $\lambda_0$ its wavelength in a vacuum, while n represents the ratio of refractive index $n_2/n_1$. The number of contact reflections within the internal reflectance element is given by:

$$N = \frac{1}{2} L \cot \phi / t \quad [4]$$

where L is the length of the optical window or carrier 20 and t its thickness. The surface modification chemistry and optical alignment are arranged in such a fashion that the chemical changes in the course of the measurement are well covered by the evanescent wave propagation and captured by an optical detector 25.

Figure 3:
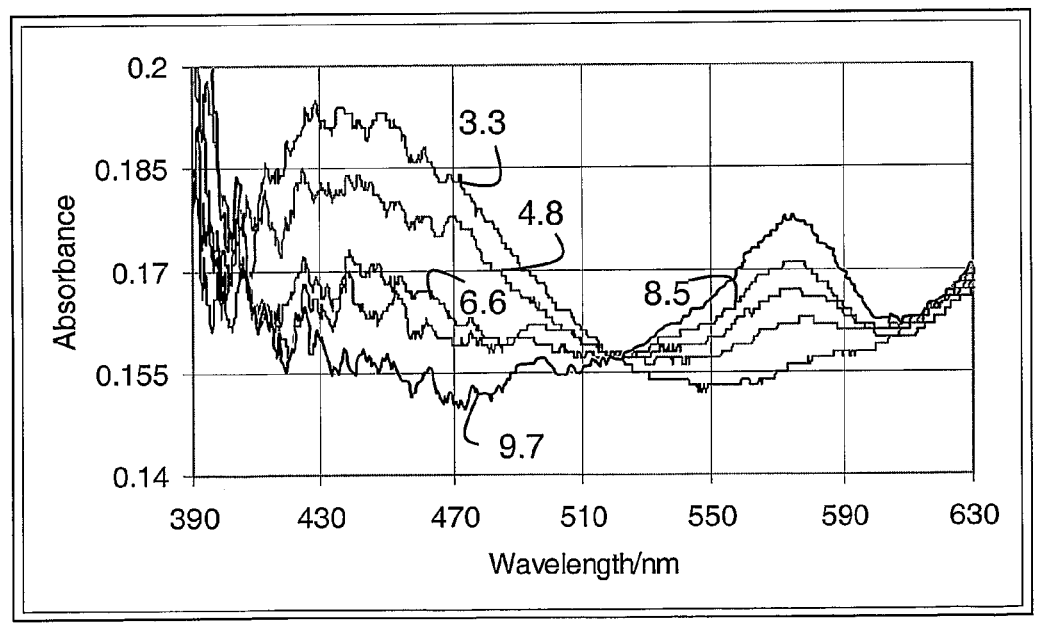
FIG. 3 shows absorbance spectra at different levels of pH.

These devices respond rapidly to the chemical changes at the interface, due to the absence of the hindrance of conventional protective membrane. In the example of FIG. 3, the absorbance ratio of the two bands that represent the protonated and deprotonated form of the dye, respectively, is measured. The spectra of FIG. 3 are taken at pH values of 3.3, 4.8, 6.6, 8.5, and 9.7, respectively. With increasing pH, the absorbance at 440 nm shrinks while at 575 nm it increases. Using the dimensionless A(575)/A(440) ratio, the pH measurement is made insensitive to the absolute values of chromophore concentration or optical path length. This approach leads to measurements independent of total dye concentration and optical path length of the device; the measurements also show reduced temperature dependence.

Figure 4:
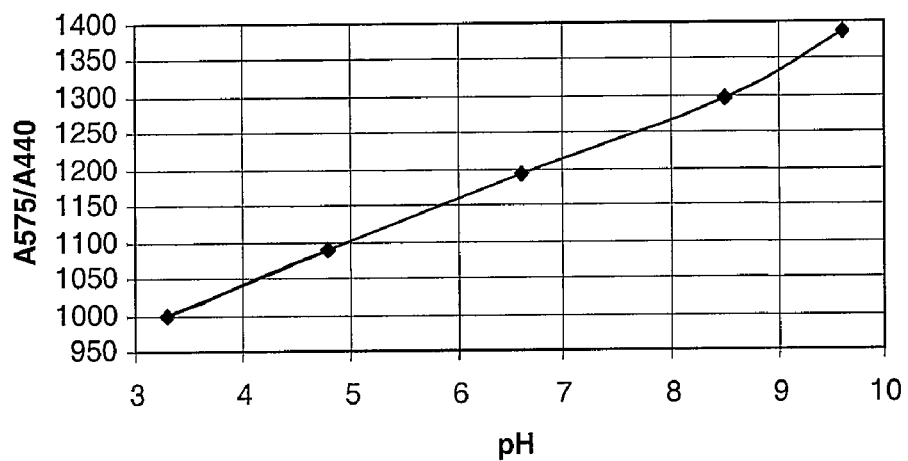
FIG. 4 is a plot of a calibration curve using the ratio of two absorbance peaks in the spectra (A575/A440) of FIG. 3.

As shown in the graph of FIG. 4, the measurement of the ratio of two different bands appears to result in a near linear dynamic range of >pKa±3.5 units for a phenolphthalein derivative.

The pH measurement can be readily used to measure the concentration of other species, such as $CO_2$, another important species in borehole fluids, according to the following formula:

$$pH = pK_1 + \text{Log}([CO_2] - 0.0449\alpha P_{CO2})/0.0449\alpha P_{CO2} \quad [5]$$

where $K_1$ is the apparent acid constant, $[CO_2]$ is the total concentration of all carbonate species and free carbon dioxide, the factor 0.049 (mol/L) the reciprocal molar volume under normal conditions, $\alpha$ the Bunsen absorption coefficient and $P_{CO2}$ the partial pressure in bar.

An alternative temperature-dependent formula is:

$$pH = 7.3232 + (\text{Log}[HCO_3^-] - 3) - \text{Log}\, P_{CO2} - ((160-T)\, 0.0041) \quad [6]$$

where $[HCO_3^-]$ is measured in mg/L, $P_{CO2}$ in psi and T in ° F.

Figure 5:
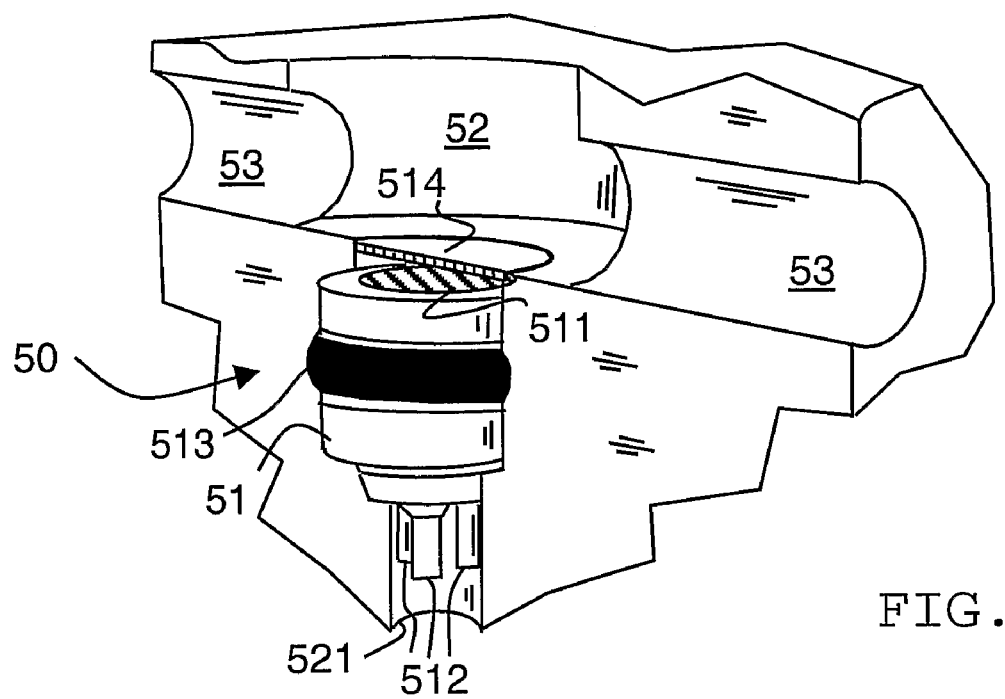
FIG. 5 is a perspective view, partially cut-away, of a sensor in accordance with an example of the present invention in a downhole tool.

A sensor assembly 50 using the electrode configuration as shown in FIG. 2, can be coupled to a flowline 53 in a manner described in FIG. 5. The body 51 of the sensor is fixed into the end section of an opening 52. The body carries the optical interface 511 with the chromophores and contacts 512 that provide connection points for power supply and signal feed-through from and to the sensor through a small channel 521 at the bottom of the opening 52. A sealing ring 513 protects the contact points and electronics from the wellbore fluid that passes under operation conditions through the sample channel 53. The active surface may be exposed directly to the fluid flow, or alternative and as shown, a permeable membrane 514 may protect the optical interface 511 from direct contact with the fluid passing through the flowline 53.

The sensors of the present invention such as described in the example of FIG. 5 or alternatives thereof can be used in a variety of measurements, some of which are described below in greater detail.

In the following various possible downhole applications of the novel sensor are described making reference to FIGS. 6-8.

Figure 6:
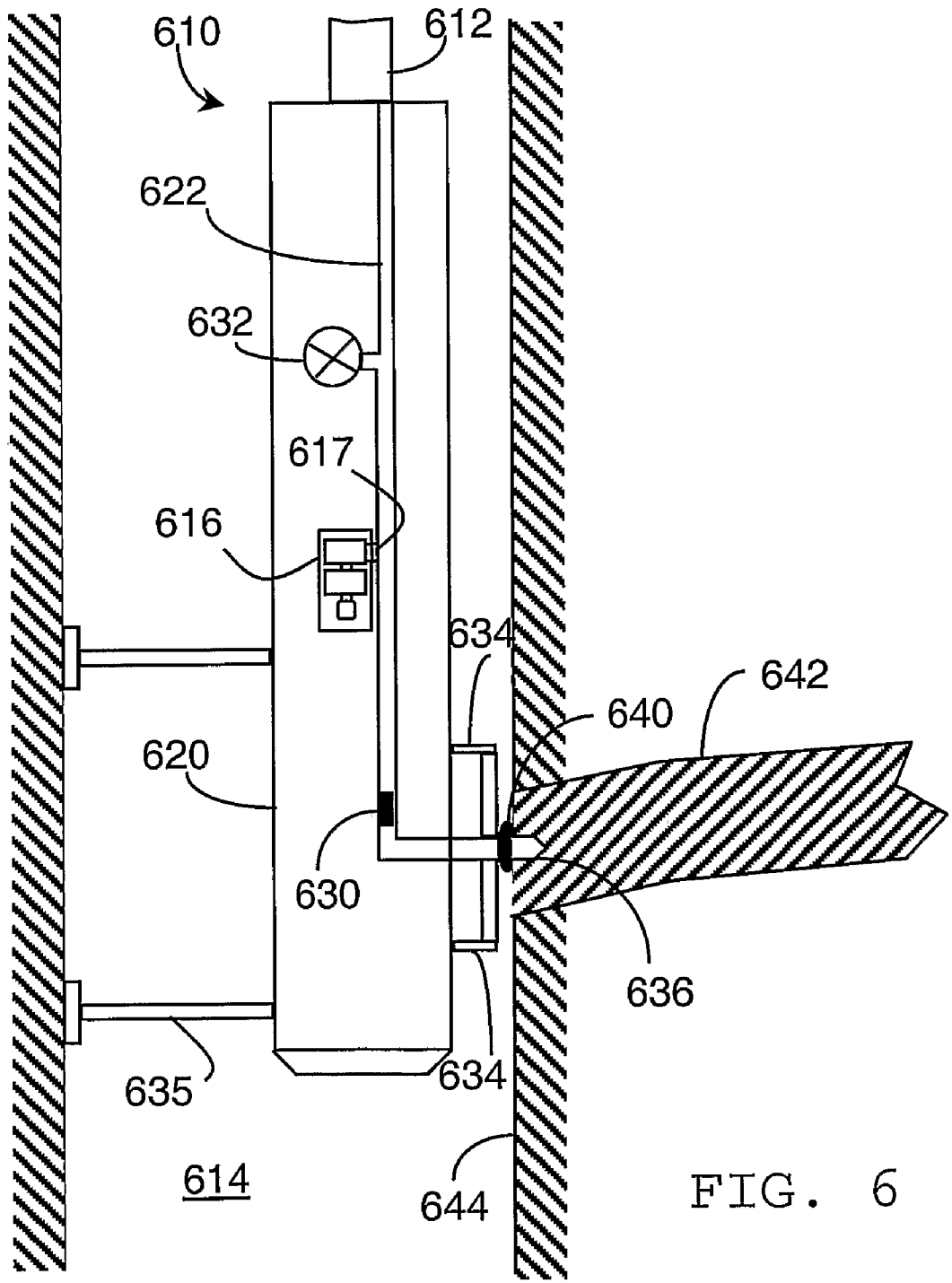
FIG. 6 illustrates an example of a sensor in accordance with the invention as part of a wireline formation testing apparatus in a wellbore.

In FIG. 6, there is shown a formation testing apparatus 610 held on a wireline 612 within a wellbore 614. The apparatus 610 is a well-known modular dynamic tester (MDT, Mark of Schlumberger) as described in the co-owned U.S. Pat. No. 3,859,851 to Urbanosky U.S. Pat. No. 3,780,575 to Urbanosky and U.S. Pat. No. 4,994,671 to Safinya et al., with this known tester being modified by introduction of a sensor 616 as described in detail above (FIG. 5). The modular dynamics tester comprises body 620 approximately 30 m long and containing a main flowline bus or conduit 622. The analysing tool 616 communicates with the flowline 622 via opening 617. In addition to the novel sensor system 616, the testing apparatus comprises an optical fluid analyser 630 within the lower part of the flowline 622. The flow through the flowline 622 is driven by means of a pump 632 located towards the upper end of the flowline 622. Hydraulic arms 634 and counterarms 635 are attached external to the body 620 and carry a sample probe tip 636 for sampling fluid. The base of the probing tip 636 is isolated from the wellbore 614 by an o-ring 640, or other sealing devices, e.g. packers.

Before completion of a well, the modular dynamics tester is lowered into the well on the wireline 612. After reaching a target depth, i.e., the layer 642 of the formation which is to be sampled, the hydraulic arms 634 are extended to engage the sample probe tip 636 with the formation. The o-ring 640 at the base of the sample probe 636 forms a seal between the side of the wellbore 644 and the formation 642 into which the probe 636 is inserted and prevents the sample probe 636 from acquiring fluid directly from the borehole 614.

Once the sample probe 636 is inserted into the formation 642, an electrical signal is passed down the wireline 612 from the surface so as to start the pump 632 and the sensor systems 616 and 630 to begin sampling of a sample of fluid from the formation 642. The sensor 616 is adapted to measure the concentration of protons of the formation effluent.

A bottle (not shown) within the MDT tool may be filled initially with a calibration solution to ensure in-situ (downhole) calibration of sensors. The MDT module may also contain a tank with a greater volume of calibration solution and/or of cleaning solution which may periodically be pumped through the sensor volume for cleaning and re-calibration purposes.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

Figure 7:
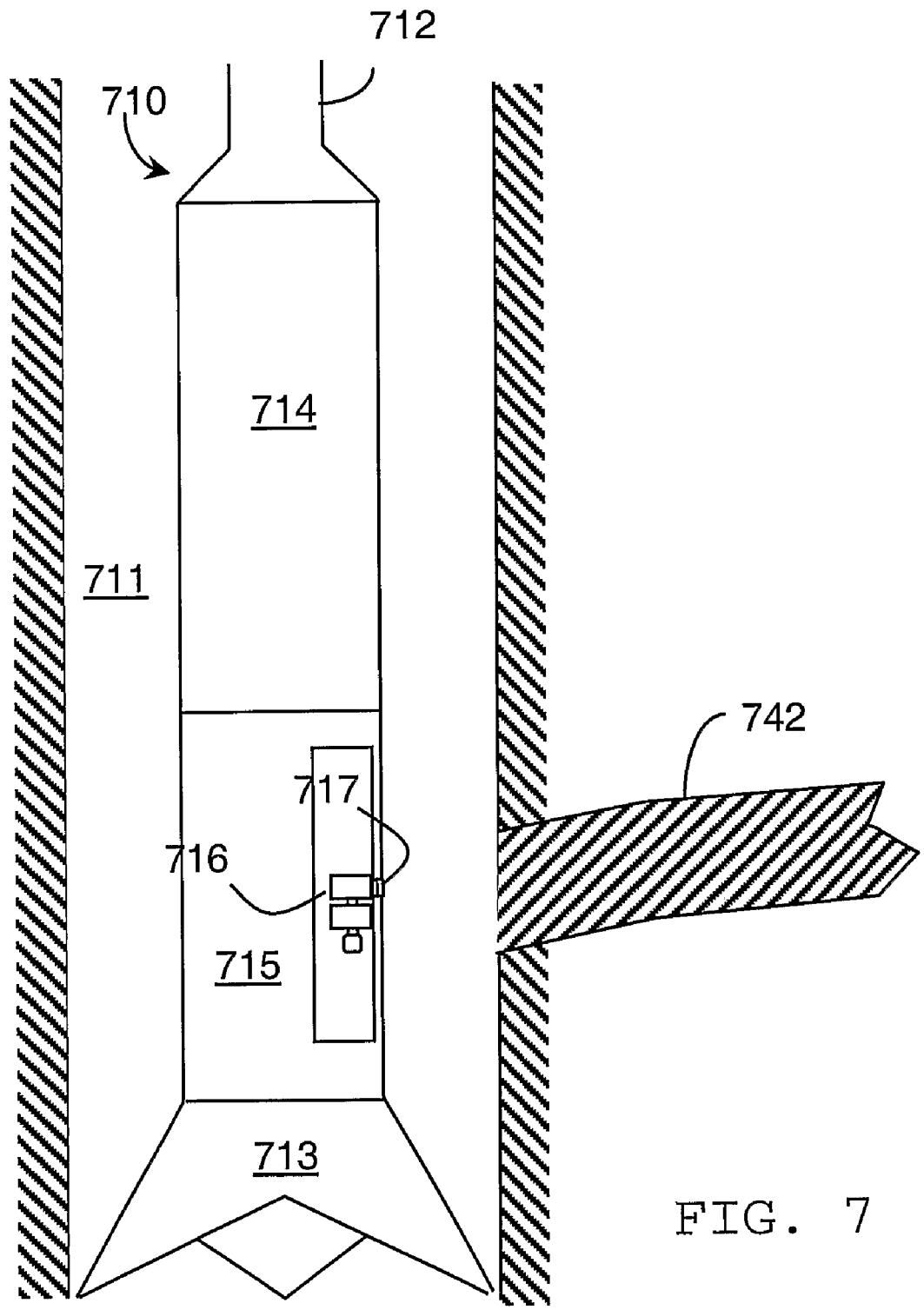
FIG. 7 shows a wellbore and the lower part of a drill string including the bottom-hole-assembly, with a sensor in accordance with the invention.

In FIG. 7, there is shown a wellbore 711 and the lower part of a drill string 712 including the bottom-hole-assembly (BHA) 710. The BHA carries at its apex the drill bit 713. It includes further drill collars that are used to mount additional equipment such as a telemetry sub 714 and a sensor sub 715. The telemetry sub provides a telemetry link to the surface, for example via mud-pulse telemetry. The sensor sub includes a novel pH sensor 716 as described above. The sensor units 716 collects fluids from the wellbore and hence from oil-bearing layers such as layer 742 via a small recess 717 protected from debris and other particles by a metal mesh.

During drilling operation wellbore fluid enters the recess 717 and is subsequently analyzed using sensor unit 716. The results are transmitted from the data acquisition unit to the telemetry unit 714, converted into telemetry signals and transmitted to the surface.

Figure 8:
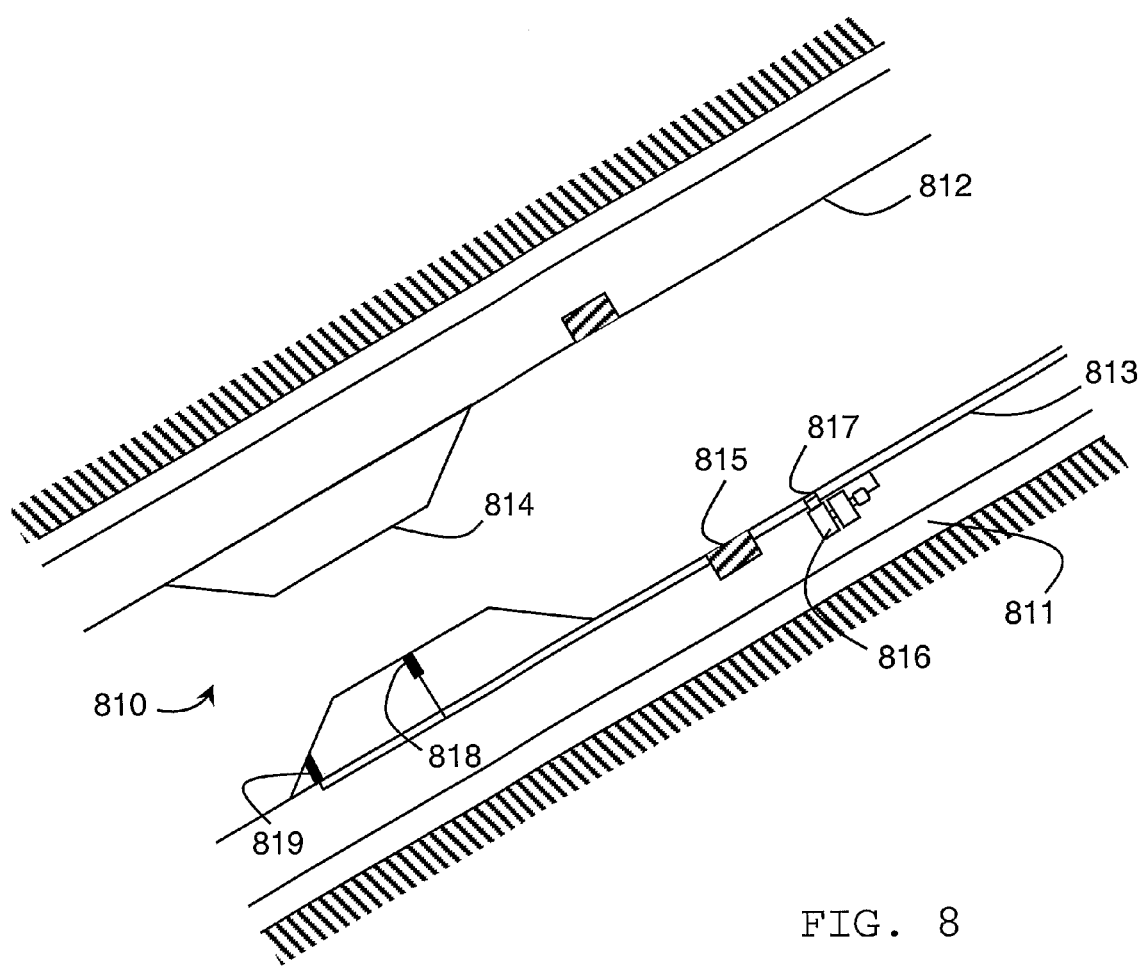
FIG. 8 shows a sensor located downstream of a venturi-type flowmeter in accordance with the invention.

A third application is illustrated in FIG. 8. It shows a Venturi-type flowmeter 810, as well known in the industry and described for example in the U.S. Pat. No. 5,736,650. Mounted on production tubing or casing 812, the flowmeter is installed at a location within the well 811 with a wired connection 813 to the surface following known procedures as disclosed for example in the U.S. Pat. No. 5,829,520.

The flowmeter consists essentially of a constriction or throat 814 and two pressure taps 818, 819 located conventionally at the entrance and the position of maximum constriction, respectively. Usually the Venturi flowmeter is combined with a densiometer 815 located further up- or downstream.

The novel pH sensor 816 is preferably located downstream from the Venturi to take advantage of the mixing effect the Venturi has on the flow. A recess 817 protected by a metal mesh provides an inlet to the unit.

During production wellbore fluid enters the recess 817 and is subsequently analyzed using sensor unit 816. The results are transmitted from the data acquisition unit to the surface via wires 813.

A sensor in accordance with the present invention will also be applicable as a formation evaluation probe. This can have direct impact on the evaluation of the distribution, size and properties of the different pay zones with a given reservoir. It can also be used in production logging process as a diagnosis of, for example, hydrogen sulphide.

Various embodiments and applications of the invention have been described. The descriptions are intended to be illustrative of the present invention. It will be apparent to those skilled in the art that modifications may be made to the invention as described without departing from the scope of the claims set out below.

The invention claimed is:

1. A downhole tool for measuring at least one characteristic of a wellbore fluid, comprising a pH sensor comprising:
   a substrate;
   chromophores sensitive to changes in pH in the vicinity of said chromophores;
   bisilane agents linking the chromophores to the substrate, wherein the bisilane agents comprise two terminal Si-functional groups, and wherein a first terminal Si-functional group of the bisilane agents binds to the substrate and a second terminal Si-functional group of the bisilane agents binds to the chromophores;
   one or more molecular membranes over the chromophores; and
   an optical system configured to monitor optical properties of the chromophores.

2. The downhole tool of claim 1, wherein the bisilane agents bind a monolayer of the chromophores to the substrate.

3. The downhole tool of claim 1, wherein the one or more molecular membranes provide a hydrophobic surface.

4. The downhole tool of claim 1, wherein the one or more molecular membranes provide a hydrophilic surface.

5. The downhole tool of claim 1 wherein the optical system is adapted to monitor changes in the optical absorption in an internal reflectance mode.

6. The downhole tool of claim 1 wherein the optical system is adapted to determine the absorbance of the chromophores at two or more different wavelengths.

7. The downhole tool of claim 1 further comprising a processor receiving signals representing the absorbance of the chromophores at two or more different wavelengths as input signals and generating a signal representative of pH.

8. The downhole tool of claim 7 wherein said processor includes a conversion unit to convert pH measurements into signals representative of the concentration of a different compound.

9. The downhole tool of claim 8, wherein the compound is carbon dioxide.

10. The downhole tool of claim 1 mounted onto a downhole fluid sampling tool suspended by a wireline.

11. The downhole tool of claim 1 mounted onto a permanently installed part of the wellbore.

12. The downhole tool of claim 1 mounted onto a drill string.

13. A method of measuring pH of a wellbore fluid, comprising
providing a sensor at a downhole location, said sensor comprising:
a substrate;
chromophores sensitive to changes in pH in the vicinity of said chromophores;
bisilane agents linking the chromophores to the substrate, wherein the bisilane agents comprise two terminal Si-functional groups, and wherein a first terminal Si-functional group of the bisilane agents binds to the substrate and a second terminal Si-functional group of the bisilane agents binds to the chromophores; and
one or more molecular membranes over the chromophores;
and monitoring optical properties of the chromophores.

14. The method of claim 13, wherein the one or more molecular membranes provide a hydrophobic surface.

15. The method of claim 13, wherein the one or more molecular membranes provide a hydrophilic surface.

16. The method of claim 13 wherein monitoring of the optical properties of the chromophores comprises determining the absorbance of the chromophores at two or more different wavelengths.

17. The method of claim 13 further comprising processing signals representing the absorbance of the chromophores at two or more different wavelengths and generating a signal representative of pH.

18. The method of claim 13 further comprising processing signals representing the absorbance of the chromophores and generating a signal representative of the concentration of carbon dioxide.

* * * * *